United States Patent [19]

Hubbard et al.

[11] Patent Number: 4,898,518

[45] Date of Patent: Feb. 6, 1990

[54] SHAFT DRIVEN DISPOSABLE CENTRIFUGAL PUMP

[75] Inventors: Lloyd C. Hubbard, Deephaven; Earl W. Clausen, Eden Prarie, both of Minn.

[73] Assignee: Minnesota Mining & Manufacturing Company, St. Paul, Minn.

[21] Appl. No.: 239,526

[22] Filed: Aug. 31, 1988

[51] Int. Cl.⁴ .................. F04D 29/08; F04D 29/60
[52] U.S. Cl. .................... 417/360; 417/423.9; 417/423.11; 417/423.14; 415/230; 415/900
[58] Field of Search ............ 415/140, 900, 170.1, 415/912, 171.1, 230, 173.6; 417/360, 423.1, 423.9, 423.11, 423.12, 423.14; 403/328, 356, 383; 604/4, 151

[56] References Cited

U.S. PATENT DOCUMENTS

| Re. 28,742 | 3/1976 | Rafferty et al. | 415/90 |
|---|---|---|---|
| 851,457 | 4/1907 | Verner . | |
| 874,431 | 12/1907 | Pitkin . | |
| 1,225,805 | 5/1917 | Griepe . | |
| 2,027,505 | 1/1936 | Winkler | 286/11 |
| 2,092,351 | 9/1937 | Huntzicker | 417/423.11 |
| 2,250,348 | 7/1941 | Beier | 288/2 |
| 2,276,622 | 3/1942 | Leake | 288/2 |
| 2,373,443 | 4/1945 | Armington | 286/7 |
| 2,403,298 | 7/1946 | Payne | 286/11 |
| 2,404,816 | 7/1946 | Snyder | 251/113 |
| 2,465,625 | 3/1949 | Aue | 230/127 |
| 2,540,968 | 2/1951 | Thomas | 308/15 |
| 2,669,668 | 2/1954 | Okulitch et al. | 310/104 |
| 3,541,607 | 11/1970 | Greene | 415/112 |
| 3,576,380 | 4/1971 | Sargeant | 417/423.11 |
| 3,608,088 | 9/1971 | Dorman et al. | 3/1 |
| 3,617,151 | 11/1971 | Scroggins | 417/18 |
| 3,647,324 | 3/1972 | Rafferty et al. | 417/420 |
| 3,652,176 | 3/1972 | Walsh | 415/9 |
| 3,676,015 | 7/1972 | Hodgman, Jr. | 415/202 |
| 3,698,830 | 10/1972 | Goyne | 417/423.14 |
| 3,767,212 | 10/1973 | Ludwig | 277/25 |
| 3,864,055 | 2/1975 | Kletschka et al. | 415/1 |
| 3,901,623 | 8/1975 | Grennan | 415/141 |
| 3,957,389 | 5/1976 | Rafferty et al. | 415/1 |
| 3,966,363 | 6/1976 | Rowley et al. | 417/423.11 |
| 3,970,408 | 7/1976 | Rafferty et al. | 415/60 |
| 4,037,984 | 7/1977 | Rafferty et al. | 415/60 |
| 4,135,253 | 1/1979 | Reich et al. | 3/1.7 |
| 4,185,617 | 1/1980 | Hutchins | 128/1 D |
| 4,257,744 | 3/1981 | Watson | 416/244 R |
| 4,283,645 | 8/1981 | Hofmann | 417/420 |
| 4,304,532 | 12/1981 | McCoy | 417/420 |
| 4,402,515 | 9/1983 | Malott | 277/24 |
| 4,408,952 | 10/1983 | Schweinfurter | 415/53 T |
| 4,589,822 | 5/1986 | Clausen et al. | 415/170 A |
| 4,606,698 | 8/1986 | Clausen et al. | 415/170 A |
| 4,643,641 | 2/1987 | Clausen et al. | 415/170 A |

*Primary Examiner*—Leonard E. Smith
*Assistant Examiner*—John A. Savio, III
*Attorney, Agent, or Firm*—Kinney & Lange

[57] ABSTRACT

A disposble centrifugal pump has two parts. One part includes a blood pumping chamber and a driven impeller, while the second part includes an impeller drive to which the impeller is coupled by mechanical shaft couplings. Two seals are provided to limit exposure of the fluid being pumped to possible contaminants. The first seal provides an effective shaft seal around the impeller shaft as it leaves the pumping chamber. The second seal provides an effective seal about all outer portions of the shaft when the shaft is coupled to the impeller drive to limit migration of possible contaminants along the shaft and into the pumping chamber.

17 Claims, 3 Drawing Sheets

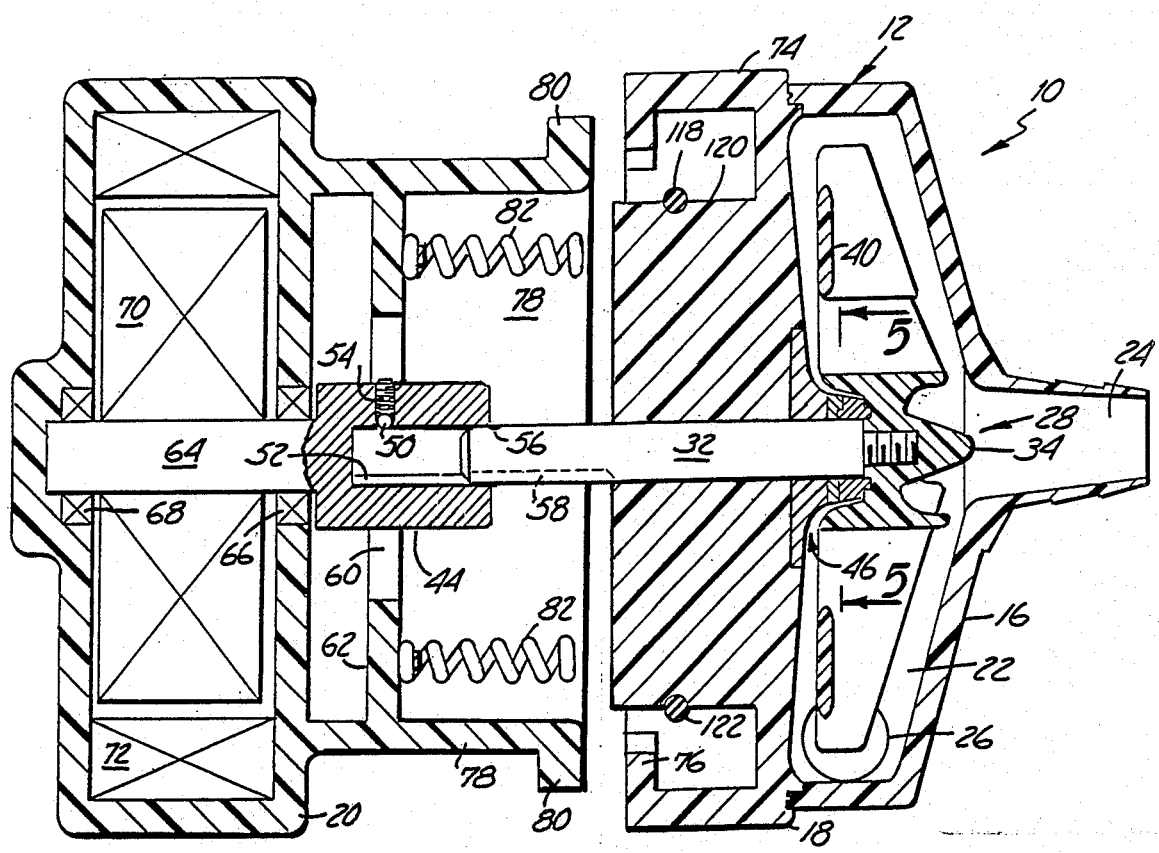
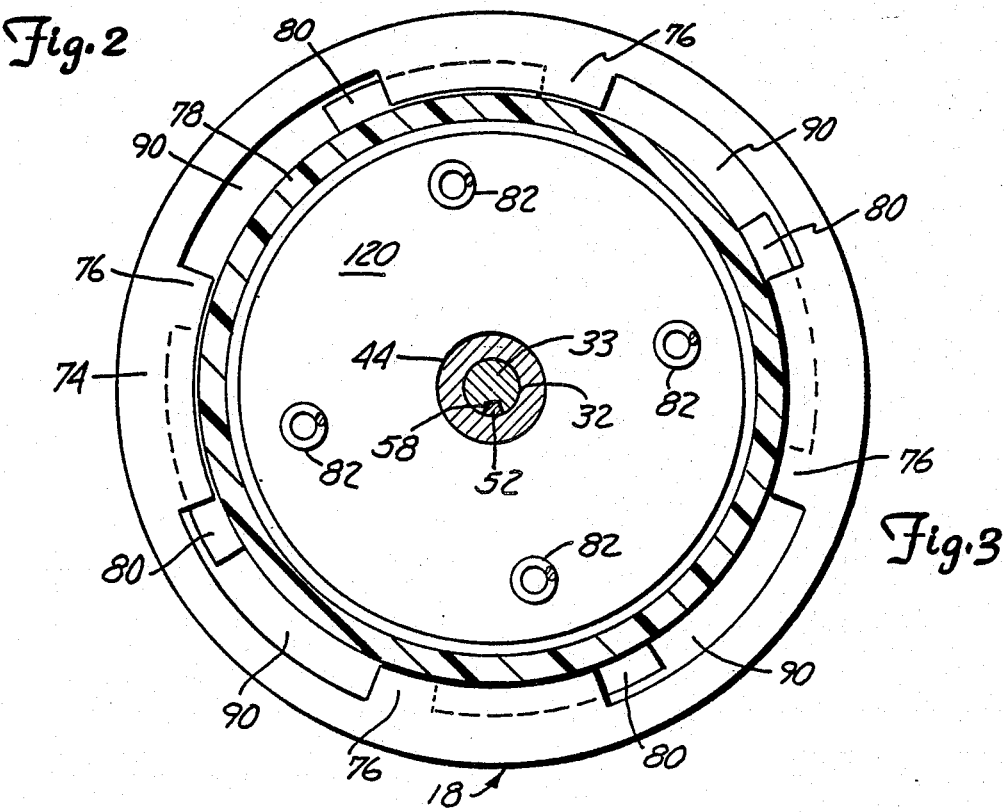
Fig. 2
Fig. 3

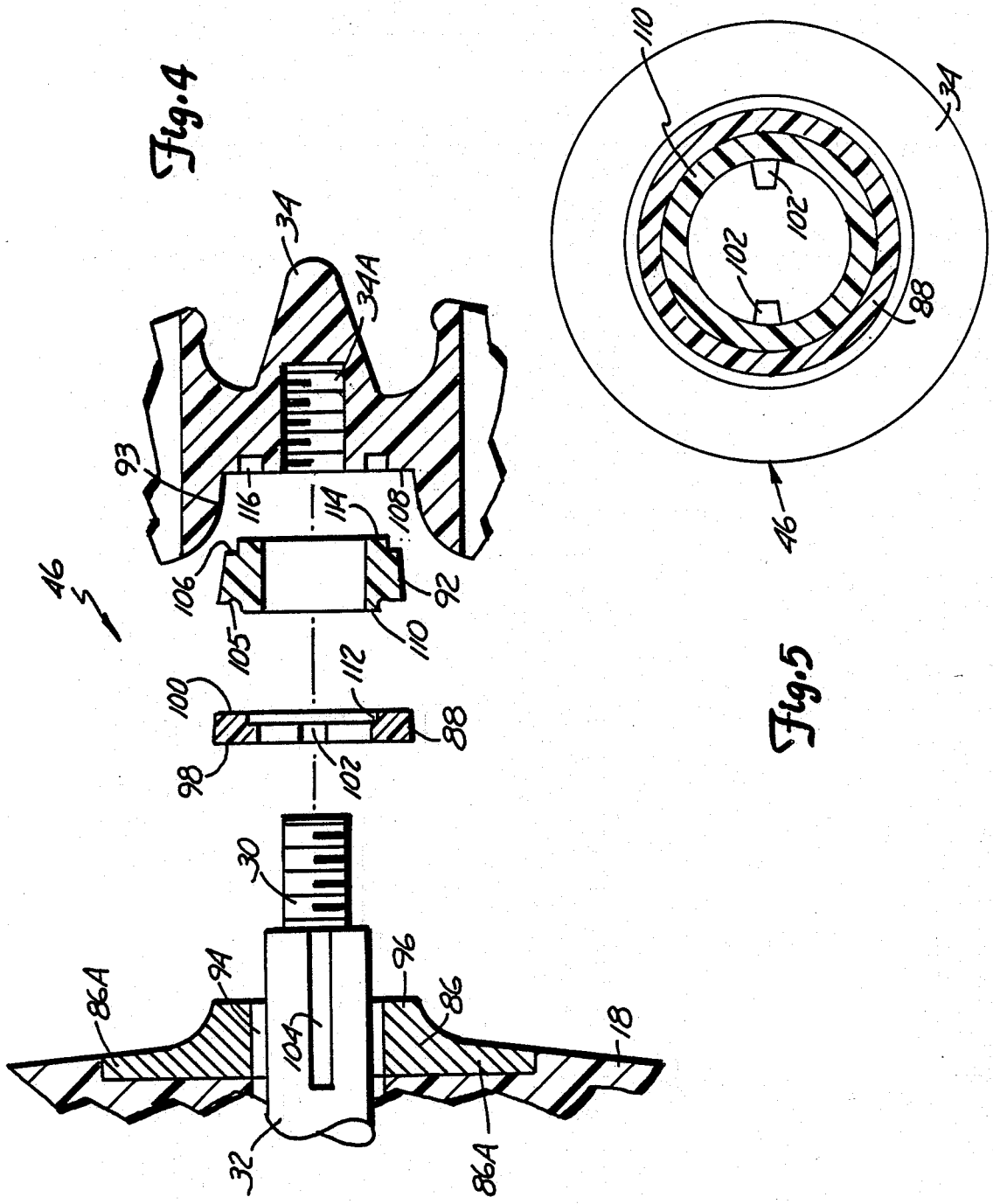

SHAFT DRIVEN DISPOSABLE CENTRIFUGAL PUMP

BACKGROUND OF THE INVENTION

1. Field of the Invention

The present invention is related to centrifugal blood pumps.

2. Description of the Prior Art

Centrifugal pumps have been use for many years to pump a wide variety of different fluid materials. In general, a centrifugal pump includes a pumping chamber with an inlet aligned with a rotational axis of the pump, an outlet adjacent the periphery of the pumping chamber, and an impeller mounted within the pumping chamber for rotation about the axis. The impeller in such pumps can be mounted on a drive shaft which extends outside the pumping chamber to a rotational drive source or the shaft can be mounted within the pumping chamber as a spindle about which the impeller rotates (rotatably driven by means other than the rotation of the shaft, such as a magnetic drive arrangement). In any case, as the impeller is rotated, it imparts centrifugal force and velocity to the fluid, thus pumping the fluid from the pump inlet to the pump outlet.

In recent years, centrifugal pumps have been used extensively for pumping blood during open heart surgery. The pumping of blood requires great care to avoid any damage to the red corpuscles, or any of the other constituents of the blood. Any practical blood pump useful as part of heart/lung bypass equipment during open heart surgery must deliver the requisite flow volumes under pressure, without damaging the blood being pumped.

In a centrifugal pump, and in particular in a centrifugal pump for pumping liquids such as blood, a fluid tight seal between the rotating part (e.g. the drive shaft) and the non-rotating part (e.g. the housing) is an important factor in the performance of the pump. It is critical that the seepage of any external fluid (gas or liquid) into the blood pumping chamber be closely controlled and minimized, specifically limiting exposure to outside air which could enter the pumping chamber.

In blood pumps which are driven by a magnetic drive arrangement, the shaft seal can be more easily isolated from exterior contamination. For example, in Dorman et al. U.S. Pat. No. 3,608,088 a magnetic rotor is connected to an impeller and is sealed within the same housing as the impeller with the blood acting as a lubricant. In Rafferty et al. U.S. Pat. No. 3,647,324, the impeller is not shaft driven. The impeller is provided with magnetic components which coact with windings positioned concentrically about the impeller in the pump housing. In Reich et al. U.S. Pat. No. 4,135,253 the impeller is shafted to a magnetic rotor. Saline solution is directed past the rotor to lubricate it, with the saline solution being maintained at a higher pressure than the blood so that if there is leakage through a seal adjacent the impeller (between the pumping chamber and the magnetic rotor chamber), the saline solution will seep into the blood rather than vice versa.

Clausen et al. U.S. Pat. No. 4,606,698 and Clausen et al. U.S. Pat. No. 4,589,822 show a centrifugal pump having an impeller which is shaft driven via magnetic coupling. The pumping chamber is isolated from the magnetic rotor secured to the impeller shaft and the impeller shaft bearings by a shaft seal, and the chamber housing the magnetic rotor is otherwise sealed to the atmosphere to prevent the migration of contaminants (e.g., air bacteria, etc.) into the pumped blood from the outside of the pump. If a seal failure occurred in the device of these Clausen et al. patents, the quantity of air which could enter the pumping chamber is limited to that amount contained in the magnetic rotor chamber.

All of the devices of the above-mentioned patents have magnetic components imbedded in a rotating part which is attached to the pump impeller. Rotating motion is coupled magnetically to the pump impeller by placing the impeller in close proximity to a corresponding set of magnets which are attached to the rotating part of a suitable drive system or, in the case of the Rafferty et al. U.S. Pat. No. 3,647,324, by energizing the windings about the pump impeller. Recently there has been an increased emphasis on cost reduction in medical equipment and, as a result, a move to low-cost, single-use disposable equipment whenever possible. Bearings and magnetic components are relatively expensive, and thus lead to high costs for the disposable portion of a centrifugal blood pump which is magnetically driven. The elimination of the magnetic assembly and bearings from the disposable portion of such a pump would significantly reduce the cost associated with the pump.

Essentially, two problems have stood in the way of driving a centrifugal blood pump impeller by direct connection to the drive shaft of a motor: (1) the inability to provide a shaft seal which would retain pressure integrity for the period of time required for pump use, and (2) the danger of potentially fatal consequences, because of air inspiration, should that seal fail.

It has been proposed that a centrifugal pump for medical use have a shaft driven impeller wherein the shaft is mechanically coupled to a drive source, as opposed to a magnetic coupling. Rafferty et al. U.S. Reissue Pat. No. Re. 28,742; Kletschka et al. U.S. Pat. No. 3,864,055; Rafferty et al. U.S. Pat. No. 3,957,389; Rafferty et al. U.S. Pat. No. 3,970,408 and Rafferty et al. U.S. Pat. No. 4,037,984 show examples of these types of pumps. None of these patents, however, discloses a satisfactory arrangement for effectively sealing the pumping chamber from external contaminants adjacent the rotating impeller shaft, or at least limiting the scope of such possible contamination if a shaft seal should fail.

SUMMARY OF THE INVENTION

The present invention is an improved centrifugal blood pump which enhances the efficiency and cost effectiveness of a disposable two-part blood pump, wherein one part includes a blood pumping chamber and driven impeller and a second part includes impeller drive means. The impeller is coupled to the drive means by mechanical shaft couplings, but the present invention provides not only an effective shaft seal around the impeller shaft as it leaves the pumping chamber, but also a second seal about all outer portions of the shaft when the shaft is coupled to the drive means to limit the exposure of possible contaminants from migrating along the shaft and into the pumping chamber.

A centrifugal pump for pumping a biological fluid such as blood includes an impeller housing having a fluid pumping chamber with at least one inlet and one outlet connected to the pumping chamber. An impeller shaft having first and second opposite ends extends rotatably through a wall of the impeller housing with its first end in the pumping chamber. An impeller is mounted on the first end of the impeller shaft for rotation therewith in the pumping chamber. First seal means are provided to effect a fluid tight seal in the wall of the impeller housing adjacent the impeller shaft and prevent fluid or gas from leaking into or out of the pumping chamber along the impeller shaft. Impeller drive means are provided to releasably and operably engage the second end of the impeller shaft outside of the pumping chamber of the impeller housing for rotating the shaft and impeller mounted thereon. When the impeller shaft and impeller drive means are engaged, those portions of the impeller shaft outside of the pumping chamber are surrounded by containment means which creates a shaft seal chamber. Second seal means are provided to effect a fluid-tight seal for the shaft seal chamber to prevent fluid or gas from leaking into or out of the shaft seal chamber when the impeller shaft and impeller drive means are engaged.

In a preferred embodiment, the centrifugal pump of the present invention is configured as a two-part pump, with the impeller housing, impeller shaft, impeller and first seal means forming a disposable pump unit which is separable from a reusable drive unit that includes the impeller drive means. Preferably, the containment means comprises an annular collar on an exterior side of the impeller housing with the collar being coaxially positioned about the impeller shaft. The containment means also includes a cylindrical sleeve having the impeller drive means mounted at a first closed end thereof with the sleeve aligned to coaxially surround the impeller shaft outside of the pumping chamber. An open second end of the sleeve cooperates with the annular collar and exterior side of the impeller housing to form a shaft seal chamber when the second end of the sleeve and annular collar are placed in an engaged relation. The impeller shaft and impeller drive means are also engaged when the second end of the sleeve and annular collar are placed in their engaged relation, which is preferably effected by providing the annular collar and second end of the sleeve with cooperating bayonet mount components. The second seal is an O-ring type seal positioned between the impeller housing and the cylindrical sleeve, proximate the second end of the sleeve. Preferably, the impeller housing has a cylindrical portion extending outwardly therefrom coaxially about the impeller shaft. This cylindrical portion has an outer diameter slightly smaller than an inner diameter of the cylindrical sleeve and the O-ring is positioned between the cylindrical portion of the impeller housing and the cylindrical sleeve.

In a preferred embodiment, the impeller shaft is movable axially relative to the impeller housing wall. When the impeller shaft and impeller drive means are engaged, the impeller drive means is coupled to the impeller shaft for axial movement therewith. The centrifugal pump has a drive housing for the impeller drive means, and means are provided for releasably coupling the impeller housing to the drive housing when the impeller shaft and impeller drive means are engaged. Bias means urge the impeller housing away from the drive housing axially along the impeller shaft when the impeller housing and drive housing are in coupled alignment.

BRIEF DESCRIPTION OF THE DRAWINGS

FIG. 2 shows the shaft driven centrifugal pump where the disposable pump unit is separated from the reusable drive unit.

FIG. 3 shows a sectional view along line 3—3 of FIG. 1.

FIG. 4 shows an exploded view of the first fluid-tight seal, with some parts shown in section and some parts broken away for clarity.

FIG. 5 shows a sectional view along line 5—5 of FIG. 2, with some components not shown for clarity.

DETAILED DESCRIPTION OF THE PREFERRED EMBODIMENTS

Figure 1:
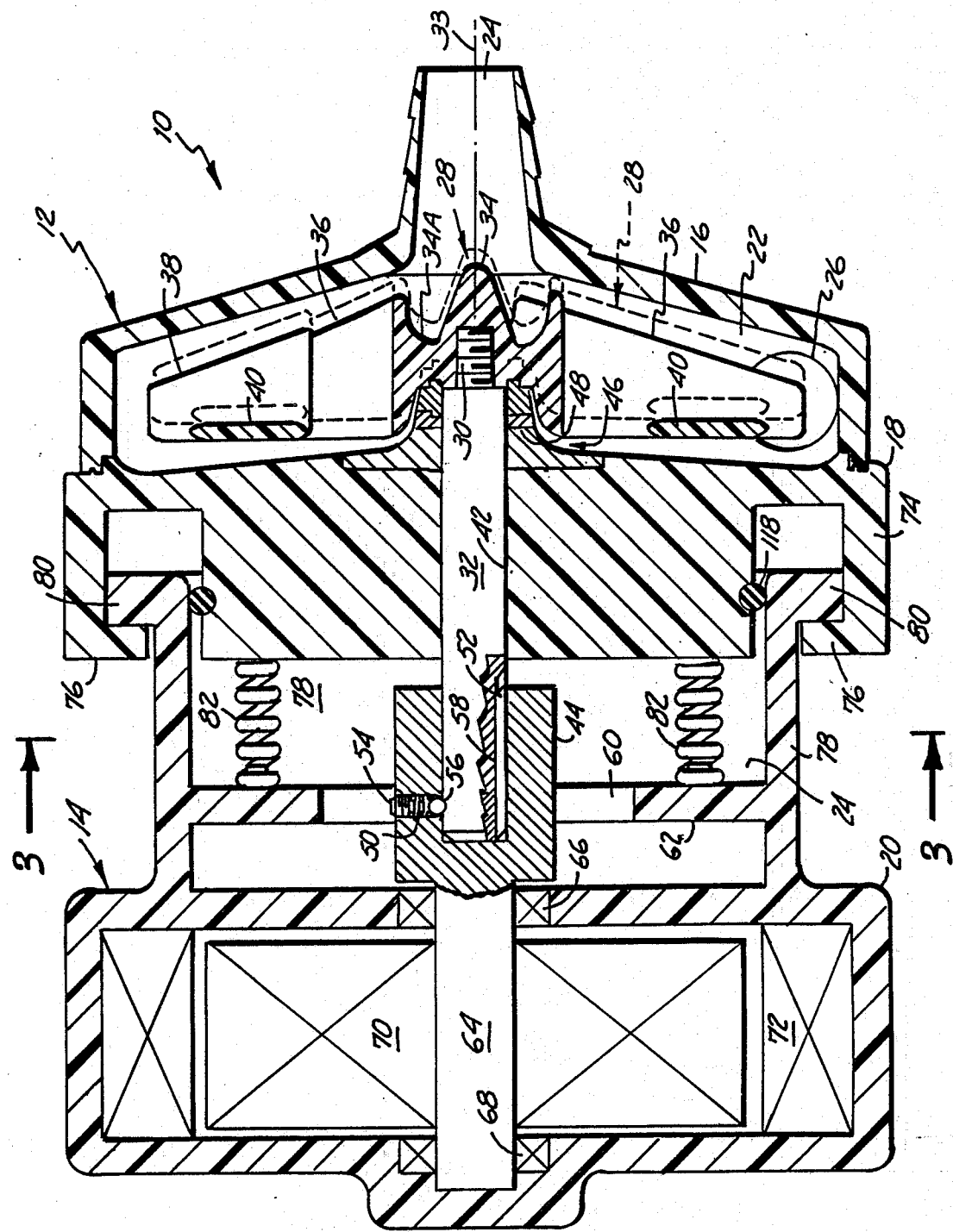
FIG. 1 shows a side sectional view of a shaft driven centrifugal pump.

FIG. 1 shows a centrifugal pump 10 which is connected for operation. The centrifugal pump 10 has a disposable pump unit 12 which is engaged with a reusable drive unit 14 in a bayonet-type connection. The disposable pump unit 12 includes a first pump housing 16 and a second pump housing 18. The reusable drive unit 14 includes a drive housing 20. The first and second pump housings 16 and 18, respectively, are sealed to define a pumping chamber 2. When the disposable pump unit 12 and reusable drive unit 14 are connected, as shown in FIG. 1, the second pump housing 18 and the drive housing 20 are sealed to define a shaft seal chamber 24.

The first pump housing 16 includes an axially aligned pump inlet 24 and a tangential pump outlet 26. Blood or other fluid is received at the inlet 24 and is pumped to the outlet 26 by rotation of an impeller 28 within the pumping chamber 22.

The impeller 28 is mounted on a threaded outer end 30 of a shaft 32, and is rotated about an axis 33 defined by the axial center of the shaft 32. The impeller 28 includes a conical shaped impeller hub 34 (with internal threads 34A for engaging the threaded outer end 30), a plurality of long blades 36, a plurality of short blades 38, and a circular flange 40.

The long blades 36 are attached at their inner ends to the impeller hub 34. The flange 40 is attached to and is supported by the long blades 36. The short blades 38 are supported by the flange 40. In this particular embodiment, the long and short blades 36 and 38 are alternatively spaced about the circumference of the impeller 28.

The shaft 32 extends away from the pumping chamber 22 through a bore 42 in the second impeller housing 18 where it engages a drive socket 44 when the disposable pump unit 12 and the reusable drive unit 14 are connected as shown in FIG. 1. In order to prevent contaminants from migrating out of the shaft seal chamber 24 along the shaft 32 through the bore 42 and into the pumping chamber 22, a first fluid tight seal 46 (as will be described in greater detail) is formed between the pumping chamber 22 and the bore 42 at a seal interface 48.

When the disposable pump unit 12 and the reusable drive unit 14 are connected as shown in FIG. 1, the shaft 32 is coupled to the drive socket 44 by a detent 50 and a key 52. The detent 50 provides for proper axial positioning of the shaft 32 with respect to the drive socket 44. When the shaft 32 is coaxially inserted within the drive socket 44 to the proper axial position, a spring 54 urges the detent 50 into a notch 56 in the shaft 32 thereby holding the shaft 32 in proper axial position with respect to the drive socket 44.

Proper radial positioning of the shaft 32 with respect to the drive socket 44 is achieved by the key 52 of the drive socket 44 and a keyway 58 in the shaft 32. Before the shaft 32 is coaxially inserted into the drive socket 44, the shaft 32 must be radially aligned with the drive socket 44 such that the key 52 will engage the keyway 58. Therefore, the shaft 32 may only be inserted into the drive socket 44 when the shaft 32 is properly radially aligned with respect to the drive socket 44.

The drive socket 44 extends away from the lower impeller housing 18 through an aperture 60 in a spring support plate 62. The drive socket 44 is fixed to a drive shaft 64 which is rotatably engaged with the drive housing 20 at a first set of bearings 66 and a second set of bearings 68, both of which are press fit into the drive housing 20.

The drive shaft 64 is fixed to a rotor 70. A stator 72 is energized and, as is well known in the art, the interaction of the magnetic fields of the rotor 70 and the stator 72 cause rotation of the rotor 70, along with the drive shaft 64, the drive socket 44, the shaft 32, and the impeller 28 with respect to the first impeller housing 16, the second impeller housing 18, and the drive housing 20.

UNIT COUPLING

The disposable pump unit 12 and the reusable drive unit 14 are coupled by an annular bayonet-type connection. An annular collar 74, which is an integral part of the second pump housing 18, forms a coaxial outer periphery of second housing 18. A plurality of feet 76 extend radially inward from the annular collar 74. Additionally, the drive housing 20 has a cylindrical sleeve 78 which extends axially away from the rotor 70 and the stator 72 and which has a diameter smaller than the diameter of the annular collar 74. The cylindrical sleeve 78 also has a plurality of feet 80 disposed about its periphery, with the feet 80 extending radially outwardly from the cylindrical sleeve 78.

FIG. 2 shows the disposable pump unit 12 and the reusable drive unit 14 in an uncoupled arrangement. In order to couple the disposable pump unit 12 and the reusable drive unit 14 (as shown in FIG. 1), the radially extending feet 76 and 80 must first be properly positioned relative to one another.

The relative positioning of radially extending feet 76 and 80 is seen in FIG. 3. In a preferred embodiment, four radially extending feet 76 and four radially extending feet 80 are disposed about the annular collar 74 and the cylindrical sleeve 78, respectively. The radially extending feet 76 are disposed about the annular collar 74 leaving several arc-shaped gaps 90. The gaps 90 are aligned with the radially extending feet 80. Then, in order to couple the disposable pump unit 12 to the reusable drive unit 14, the cylindrical sleeve 78 is coaxially inserted into the annular collar 74 by moving the disposable pump unit 12 toward the reusable drive unit 14, compressing a plurality of axially extending springs 82 until the radially extending feet 80 pass through the arc-shaped gaps 90. When the disposable pump unit 12 has been moved toward the reusable drive unit 14 enough so that the radially extending feet 80 pass through the arc-shaped gaps 90, the disposable pump unit 12 is then rotated about the axis 33 with respect to the reusable drive unit 14. The disposable pump unit 12 is rotated until the radially extending feet 76 and 80 overlap and form at least a partially interlocking interconnection, as seen in FIG. 3. Preferably, the radially extending feet 76 and 80 are rotated with respect to one another until they completely overlap. With the pump unit 12 and drive unit 14 coupled in this manner (as seen in FIG. 1), the springs 82 urge the disposable pump unit 12 away from the reusable drive unit 14, thereby causing the radially extending feet 76 and 80 to remain in a frictional, interlocking connection.

To disconnect the disposable pump unit 12 from the reusable drive unit 14, the procedure described above is reversed. Then, the disposable pump unit 12 may be axially separated from the reusable drive unit 14, as shown in FIG. 2.

SEALS

In the present invention, two fluid tight seals are used to prevent contaminants from migrating along the shaft 32 into the pumping chamber 22. A first fluid tight seal 46 seals the pumping chamber 22 from the bore 42 of the second impeller housing 18 at the seal interface 48. The first fluid tight seal 46, shown in an exploded view in FIG. 4, is formed by a seal stator 86, a seal rotor 88, and a resilient elastomer spring 92. The first fluid tight seal 46 is tapered to conform to the taper 93 of the impeller hub 34. The first fluid tight seal 46 provides the seal interface 48 between the seal stator 86 and the seal rotor 88. The seal rotor 88 is generally perpendicular to the axis 33 of the shaft 32 and is located at an intermediate position between the second pump housing 18 and the hub 34. The location of the seal interface 48 is in a high fluid flow area, which increases cooling effects and improves dissipation of heat caused by friction at the seal interface 48.

In the preferred embodiment of the present invention the seal stator 86 is fixed to the second pump housing 18, and is a high thermal conductivity material (such as nickel-plated aluminum). The seal stator 86 has an aperture 94 which is axially aligned with the shaft 32 and is of sufficient diameter so that the shaft 32 does not contact the seal stator 86. An upper face 96 of the seal stator 86, and a lower face 98 of the seal rotor 88 define the seal interface 48 which is generally perpendicular to the axis 33 of the shaft 32.

The seal stator 86 has a flange 86A at its lower end which extends outward in a radial direction from the axis 33 and generally conforms to the surface of the second impeller housing 18 at a lower end of the pumping chamber 22. The flange 86A provides a large surface area for the seal stator 86, thus increasing the ability of the seal stator 86 to transfer heat generated at the seal interface 48.

The seal rotor 88 is positioned on the shaft 32 adjacent the seal stator 86. As discussed above, the lower face 98 of the seal rotor 88 engages the upper face 96 of the seal stator 86 to define the seal interface 48. An upper face 100 of the seal rotor 88 engages the spring 92. The seal rotor 88 has a pair of inwardly projecting keys 102, also shown in FIG. 5, which engage a pair of axially extending keyways 104 on the shaft 32 so that the seal rotor 88 can move in the axial direction and yet rotate with the shaft 32. Such a key arrangement may not be necessary if, by frictional fit or bonding, the seal rotor 88 is driven by the spring 92 to rotate therewith. In a preferred embodiment, the seal rotor 88 is a low friction polymer material such as nylon.

The spring 92 is an elastomer (such as silicon rubber) ring which is mounted coaxially on the shaft 32 between the impeller hub 34 and the seal rotor 88. A lower spring face 105 of the spring 92 engages the upper face 100 of the seal rotor 88, and an upper spring face 106 engages a lower hub face 108 of the hub 34. The elastomer spring 92 is maintained under compression by the hub 34, which is threaded at the threads 34A and is in a threaded engagement with the threaded end 30 of the shaft 32, so that it urges the seal rotor 88 in an axial direction into engagement with the seal stator 86. This compression is accomplished by the springs 82 urging the second pump housing 18 away from the drive housing 20 while the detent 50 and the drive socket 44 keep the shaft 32 from moving axially, thereby establishing a desired pressure between the upper face 96 and the lower face 98 of the seal at seal interface 48. The setting of the desired pressure between the upper face 96 and lower face 98 of the seal can also be accomplished by other means. For example, the motor of the drive housing 20 can be of the type which indexes axially when actuated, thus pulling the shaft 32 axially away from the impeller housing 18 when the motor is started (a "Bendix-type" starter motor arrangement). Alternatively, a shaft could be employed which disengages through a pinion arrangement when the motor is turned on and off axially.

The spring 92 preferably has a first annular spring rib 110 which is positioned in an annular rotor groove 112 of the seal rotor 88. The spring 92 also preferably has a second annular spring rib 114 which is positioned in an annular hub groove 116 of the hub 34. The first and second spring ribs 110 and 114, respectively, help to maintain an axial alignment of spring 92 so that an essentially uniform axial force is applied to the seal rotor 88. In another embodiment (not shown), the resilient elastomer spring is positioned between the seal stator and the second impeller housing (rather than between the seal stator and the hub) and the seal stator is fixed to the hub to effectuate the sealing of the pumping chamber about the shaft.

When the disposable pump unit 12 is coupled to the reusable drive unit 14, as shown in FIG. 1 (i.e., when the bayonet-type connection is made), the shaft 32 is inserted into drive socket 44 until it is locked in place by detent 50, notch 56, key 52 and keyway 58 as described earlier. As the shaft 32 is inserted into drive socket 44, and as the disposable pump unit 12 is moved toward the reusable drive unit 14, the impeller 28 moves axially with respect to the first and second impeller housings 16 and 18, respectively, to the position shown in phantom in FIG. 1. When the impeller 28 engages the first impeller housing 16, as shown in phantom in FIG. 1, the shaft 32 is urged into the locked position in the drive socket 44. Once the shaft 32 is locked into the drive socket 44, and once the bayonet-type connection is made between the disposable pump unit 12 and the reusable drive unit 14, the springs 82 urge the first and second impeller housings 16 and 18 away from the reusable drive unit 14 such that the radially extending feet 76 and 80 are in an interlocking arrangement. This maintains the elastomer spring 92 under compression between the hub 34 such that the seal rotor 88 is urged in an axial direction into engagement with the seal stator 86.

A second seal is also used to prevent both the entrance of contaminants into the shaft seal chamber 24 and the migration of contaminants into the pumping chamber 22 along the shaft 32 in the bore 42 of the second impeller housing 18. The second seal is formed by the second impeller housing 18, the cylindrical sleeve 78, and an O-ring 118 therebetween. As shown in FIG. 2, when the disposable pump unit 12 is uncoupled from the reusable drive unit 14, the O-ring 118 is disposed about an inner cylindrical portion 120 of the second impeller housing 18 in an annular groove 122 thereof. When disposed about the cylindrical portion 120, the O-ring 118 has an outer diameter which is slightly larger than the inner diameter of the cylindrical sleeve 78 of the drive housing 20. When the disposable pump unit 12 is coupled to the reusable drive unit 14, as shown in FIG. 1, the O-ring 118 forms a rotatable, fluid tight seal between the cylindrical portion 120 of the second impeller housing 18 and the cylindrical sleeve 78 of the drive housing 20. This second seal limits the entrance of contaminants into the shaft seal chamber 24 from areas external to the coupled pump 10.

Additionally, in order for contaminants, such as liquids or gases, to leak into the pumping chamber 22 through the seal interface 48, the same amount of liquid or gas which enters pumping chamber 22 must enter shaft seal chamber 24 to equalize the pressure in the shaft seal chamber 24. The second seal formed by the O-ring 118, the cylindrical sleeve 78 and the inner cylinder 120, substantially eliminates the entrance of any gases or liquids into the shaft seal chamber 24. Therefore, the second seal helps prevent the migration of contaminants along the shaft 32 and into the pumping chamber 22.

CONCLUSION

This invention presents a shaft driven impeller in a centrifugal pump wherein the shaft is mechanically coupled to the drive source, as opposed to being magnetically coupled. Therefore, the magnetic assembly and bearings associated with magnetically coupled centrifugal pumps are eliminated from the disposable portion of the pump.

Additionally, costly bearings which had previously been incorporated into the disposable portion of the pump have been eliminated. This significantly reduces the costs associated with the pump and enhances its efficiency. Also, this invention not only provides an effective seal around the impeller shaft as it leaves the pumping chamber, but also about the region where the reusable and disposable portions of the pump are connected. Therefore, the exposure of the fluid being pumped to possible contaminants which could migrate along the shaft and into the pumping chamber is limited.

Although the present invention has been described with reference to preferred embodiments, workers skilled in the art will recognize that changes may be made in form and detail without departing from the spirit and scope of the invention.

What is claimed is:

1. In a centrifugal pump for pumping biological fluids of the type having a pumping portion and a separable drive portion with a rotatable drive shaft, the pumping portion having an impeller housing with a fluid pumping chamber therein, an impeller shaft extending rotatably through the impeller housing, an impeller mounted on the impeller shaft for rotation therewith in the pumping chamber and first seal means for providing a fluid-tight seal about the impeller shaft as it passes through the impeller housing, the improvement which comprises:

the impeller shaft being positioned and adapted to be mechanically engaged with the drive shaft of the drive portion for coupled rotation therewith when the pump and drive portions of the centrifugal pump are assembled; and means for creating a fluid-tight sealed shaft chamber surrounding those portions of the impeller shaft outside the pumping chamber when the pump and drive portions of the centrifugal pump are assembled.

2. A centrifugal pump for pumping a biological fluid such as blood, the pump comprising:

an impeller housing having a fluid pumping chamber with at least one inlet and at least one outlet connected to the pumping chamber;

an impeller shaft having first and second opposite ends, the shaft extending rotatably through a wall of the impeller housing with its first end in the pumping chamber;

an impeller mounted on the first end of the impeller shaft for rotation therewith in the pumping chamber;

first seal means for providing a fluid-tight seal in the wall of the impeller housing adjacent the impeller shaft to prevent fluid or gas from leaking into or out of the pumping chamber along the impeller shaft;

impeller drive means releasably and operably engaged to the second end of the impeller shaft outside of the pumping chamber of the impeller housing for rotating the shaft and impeller mounted thereon;

containment means for creating a shaft seal chamber surrounding those portions of the impeller shaft outside of the pumping chamber when the impeller shaft and impeller drive means are engaged; and second seal means for providing a fluid-tight seal for the shaft seal chamber to prevent fluid or gas from leaking into or out of the shaft seal chamber when the impeller shaft and impeller drive means are engaged.

3. The centrifugal pump of claim 2 wherein the impeller housing, impeller shaft, impeller and first seal means comprise a disposable pump unit which is separable from a reuseable drive unit that includes the impeller drive means.

4. The centrifugal pump of claim 2 wherein the impeller drive means comprises:

a drive motor for rotating a motor drive shaft; and coupling means for affirmatively engaging the drive shaft of the drive motor to the impeller shaft adjacent the second end thereof.

5. The centrifugal pump of claim 4 wherein the coupling means comprises:

a keyway in the impeller shaft adjacent the second end thereof; and a key mounted with respect to the drive motor shaft for engaging the keyway to couple the drive shaft and the impeller shaft together for rotation.

6. The centrifugal pump of claim 4 wherein the coupling means comprises:

a notch in the impeller shaft adjacent the second end thereof; and detent means mounted with respect to the drive motor shaft for engaging the notch to couple the drive shaft and impeller shaft together for rotation and relative axial alignment.

7. The centrifugal pump of claim 2 wherein the containment means comprises:

an annular collar on an exterior side of the impeller housing, with the collar being coaxially positioned about the impeller shaft; and a cylindrical sleeve having the impeller drive means mounted at a closed first end thereof, the sleeve being aligned to coaxially surround the impeller shaft outside of the pumping chamber with an open second end of the sleeve cooperating with the annular collar and exterior side of the impeller housing to form the shaft seal chamber when the second end of the sleeve and annular collar are placed in an engaged relation.

8. The centrifugal pump of claim 7 wherein the impeller shaft and impeller drive means are engaged when the second end of the sleeve and the annular collar are placed in their engaged relation.

9. The centrifugal pump of claim 7 herein the annular collar and the second end of the cylindrical sleeve are provided with cooperating bayonet mount components.

10. The centrifugal pump of claim 7 wherein the second seal means comprises an O-ring type seal positioned between the impeller housing and cylindrical sleeve proximate the second end of the sleeve.

11. The centrifugal pump of claim 7 wherein the impeller housing has a cylindrical portion extending outwardly therefrom coaxially about the impeller shaft, the cylindrical portion having an outer diameter slightly smaller than an inner diameter of the cylindrical sleeve, and wherein the second seal means comprises an O-ring positioned between the cylindrical portion and the cylindrical sleeve.

12. The centrifugal pump of claim 11 wherein the O-ring is mounted on the cylindrical portion of the impeller housing and is retained thereon when the cylindrical sleeve is separated from the annular collar of the impeller housing.

13. The centrifugal pump of claim 2 wherein the impeller shaft is movable axially relative to the impeller housing wall, and wherein the impeller drive means is coupled to the impeller shaft for axial movement therewith when the impeller shaft and impeller drive means are engaged, and further comprising:

a drive housing for the impeller drive means;

means for releasably coupling the impeller housing to the drive housing when the impeller shaft and impeller drive means are engaged; and bias means for urging the impeller housing away from the drive housing axially along the impeller shaft when the impeller housing and drive housing are in coupled alignment.

14. The centrifugal pump of claim 13 wherein the means for releasably coupling the impeller housing to the drive housing comprises mating bayonet mount components on opposed portions of the impeller housing and the drive housing.

15. The centrifugal pump of claim 2 wherein the impeller has a hub and wherein the first seal means comprises:

a seal stator connected to the wall of the impeller housing surrounding the impeller shaft, the seal stator defining a first seal face which is generally transverse to the impeller shaft axis and is located at an intermediate position between and spaced apart from the wall and the hub of the impeller; and a seal rotor positioned coaxially on the impeller shaft between the first seal face and the hub, the seal rotor defining a second seal face which faces the first seal face and which is generally transverse to the impeller shaft axis, the seal rotor being mounted for rotation with the impeller and being movable in the axial direction.

16. The centrifugal pump of claim 15, and further comprising:

means for establishing a desired pressure between the first and second seal faces when the impeller shaft and impeller drive means are engaged.

17. The centrifugal pump of claim 16 wherein the impeller shaft is movable axially relative to the impeller housing wall, and wherein the impeller drive means is coupled to the impeller shaft for axial movement therewith when the impeller shaft and impeller drive means are engaged, and further comprising:
- a drive housing for the impeller drive means;
- means for releasably coupling the impeller housing to the drive housing when the impeller shaft and impeller drive means are engaged; and
- bias means for urging the impeller housing away from the drive housing axially along the impeller shaft when the impeller housing and drive housing are in coupled alignment, thereby establishing the desired pressure between the first and second seal faces.

* * * * *